United States Patent [19]

Spei et al.

[11] Patent Number: 4,789,483
[45] Date of Patent: Dec. 6, 1988

[54] PROCESS FOR CONTROLLING THE BREAKING OF OIL-IN WATER EMULSIONS

[75] Inventors: Brigitte Spei, Duesseldorf; Volker Wehle, Haan, both of Fed. Rep. of Germany

[73] Assignee: Henkel Kommanditgesellschaft auf Aktien, Duesseldorf, Fed. Rep. of Germany

[21] Appl. No.: 84,660

[22] Filed: Aug. 11, 1987

[30] Foreign Application Priority Data

Aug. 11, 1986 [DE] Fed. Rep. of Germany ....... 3627199

[51] Int. Cl.⁴ ............................................. B01D 17/05
[52] U.S. Cl. .................... 210/708; 210/732; 210/745; 210/96.1
[58] Field of Search ................. 210/732, DIG. 5, 745, 210/702, 704, 705, 708, 198.1, 85, 87, 96.1, 97, 109, 205, 206, 207, 208, 209

[56] References Cited

U.S. PATENT DOCUMENTS

| | | | |
|---|---|---|---|
| 3,878,094 | 4/1975 | Conley et al. | 210/DIG. 5 |
| 3,880,526 | 4/1975 | Kobayashi et al. | 356/208 |
| 4,201,471 | 5/1980 | Pitt et al. | 356/70 |
| 4,383,927 | 5/1983 | Srivatsa | 210/732 |

FOREIGN PATENT DOCUMENTS 2440346  3/1977  Fed. Rep. of Germany .
3212734  1/1983  Fed. Rep. of Germany .
2226881  10/1975  France .

OTHER PUBLICATIONS

Bänder Bleche Rohre, vol. 11; No. 2; p. 84–92 (1970).

*Primary Examiner*—Frank Sever
*Attorney, Agent, or Firm*—Ernest G. Szoke; Henry E. Millson, Jr.

[57] ABSTRACT

Process for controlling the breaking of an oil-in-water emulsion using an organic emulsion breaker comprising the steps of:

A. adding the organic emulsion breaker to the emulsion by slow intermittent or continuous addition to produce a broken water phase;
B. continuously passing a beam of light through the broken water phase;
C. continuing the slow addition of the organic emulsion breaker to the broken water phase;
D. continuously or intermittently measuring both the unadsorbed light passing through the broken water phase and the light scattered forward by oil droplets in the broken water phase;
E. determining from the measurements in step D, the turbidity of the broken water phase; and
F. discontinuing the addition of organic breaker when the turbidity reaches a first minimum value following a maximum value.

8 Claims, 5 Drawing Sheets

4,789,483

PROCESS FOR CONTROLLING THE BREAKING OF OIL-IN WATER EMULSIONS

BACKGROUND OF THE INVENTION

1. Field of the Invention

This invention relates to a process for controlling the breaking of oil-in-water emulsions induced by organic breakers.

2. Discussion of Related Art

Oil-in-water emulsion of the type commonly used in the machining of metals, such as for example cooling and lubricating, drawing, cutting or drilling emulsions, of which the oil phase consists predominantly of natural or synthetic oils of different chemical composition and origin, not only undergo wear in use, but are also contaminated through the introduction of foreign substances. Accordingly, they have to be disposed of at regular intervals. The most important step in the—in some cases continues—disposal process is the breaking of the spent emulsions, in which as much as possible of the oil phase has to be separated from the water phase in order to be able either to work up and reuse the oil phase separated off or to be able to subject the oil phase separated off together with the water phase likewise separated off to any of the usual ecologically safe disposal processes.

The orginally used method of breaking emulsions of this type by addition of mineral salts or acids has been replaced to an increasing extent, due to its ecological disadvantages and the large amount of breaker required for complete breaking, by a breaking process in which organic breakers, generally surface-active substances, are used for breaking emulsions. The advantages of this process is that the breaker concentrations required for complete breaking are very low, for example of the order of 0.1 to 10% of the quantity of emulsion, and the breakers do not interfere with disposal of the oil phase, for example by burning. In addition, they do not cause significant pollution of the aqueous phase through the introduction of foreign substances.

The disadvantages in practical terms of using organic breakers for breaking emulsions is that overdosage of the breakers used can result in re-emulsification of the already broken emulsion. The result of this is that complete breaking of emulsions is only possible in a relatively narrow dosage range of the breakers. Below this range, breaking is incomplete, which is reflected in an undesirably high oil content in the aqueous phase. Above this range, overdosage of the breaker and the resulting reemulsification likewise lead to an increase in the oil content of the aqueous phase which, of course, is also undesirable. An additional difficulty is that the oil-in-water emulsions accumulating in practice are subject to considerable variations with respect to composition, concentration of the constituents, pH value, temperature, and other parameters. The effect of these disadvantages is that, in the practical application of surface-active substances as emulsion breakers, constant trail-and-error testing of the type and quantity of breaker is necessary to determine the optimal dosage range for the organic breaker for each particular problem.

In practice, the optimal dosage range is normally determined by visual observation of breaking behavior during the emulsion breaking process. This method of determining the optical dosage range for the breaker, i.e. the end point for the addition of the surface-active compound used as breaker, is generally carried out by adding breaker until a floating oil/sludge floc is formed. To avoid overdosages, this has to be done by adding very small quantities of breaker, which explains why the breaking of oil-in-water emulsions for visual observation of the end point takes several hours to complete.

In addition, in view of increasing efforts to automate processes of this type in the field of effluent purification, there is an increasing demand for low-maintenance, reliable automatic measuring processes.

This demand cannot be satisfied even by the conventional methods known in the prior art for measuring turbidity which have been experimentally used to control the breaking of emulsions. The impurities present in spend cooling and lubrication, deep-drawing, cutting and drilling emulsions, apart from the other adverse conditions prevailing in those emulsions, lead to incorrect measurements of a magnitude which is unacceptable in practice. In particular, discoloration caused by the oils and relatively large emulsifier-demulsifier aggregates in the aqueous phase repeatedly lead to disturbance of the measurement. Practicable processes for determining the optimal dosage range for organic breakers which give reproducible results in a short time, have not been described hitherto.

DESCRIPTION OF THE INVENTION

An object of the present invention is to provide a process for controlling the breaking of oil-in-water emulsions induced by organic breakers, in which the optimal dosage range for the organic breaker can be automatically determined in a reliable and reproducible manner. The new process is intended to be independent of impurities in the spent emulsions and to be unaffected by the color of the emulsion. In addition, the new process can be carried out fully automatically and to provide for reliable determination of the dosage end point in emulsions of the type discussed above with any of the organic breakers used in practice.

It has now surprisingly been found that the optimal dosage range for an organic breaker in the breaker of emulsions induced by organic breakers can be determined by measuring the turbidity profile as a function of the quantity of organic breaker added and using the turbidity as a measure of the quality of the broken water phase.

The emulsions broken by the process of the invention are all oil-in-water emulsions of the type accumulating, for example, in the machining of metals. These emulsions are used to cool the workpieces and tools during the particular machining operation, for example during cutting, drilling and turning, or to improve sliding and separation behavior in the non-cutting treatment of metals, for example during deep drawing. Accordingly, these emulsions are spent cooling and lubricating, deep drawing, cutting and/or drilling emulsions or corresponding emulsions produced synthetically for experimental purposes, including emulsion mixtures. The above oil-in-water emulsions are aqueous systems which can contain up to 10% of oil generally introduced from outside. However, emulsions in the context disclosed above also include the conventional alkaline, neutral or acidic degreasing and cleaning baths which accumulate, for example, in the automotive industry during the degreasing and cleaning of metal sheets.

The compounds used herein as organic breakers are known from the prior art. Cationic polymers are preferably used as breakers (demulsifiers). They preferably have a molecular weight of from 50,000 to 500,000. In practice, polyamines, polyamidoamines, polyimines, condensates of o-toluidine and formaldehyde, quaternary ammonium compounds and ionic surfactants are used with advantage, i.e. with good breaking results, even in low concentrations. Of these compounds, polyamines having an average molecular weight of from 75,000 to 200,000 or condensates of o-toluidine and formaldehyde are particularly preferred by virtue of the favorable breaking results obtained with them, even in low concentrations.

The process of the invention is described in more detail below with reference to FIG. 1.

Figure 1:
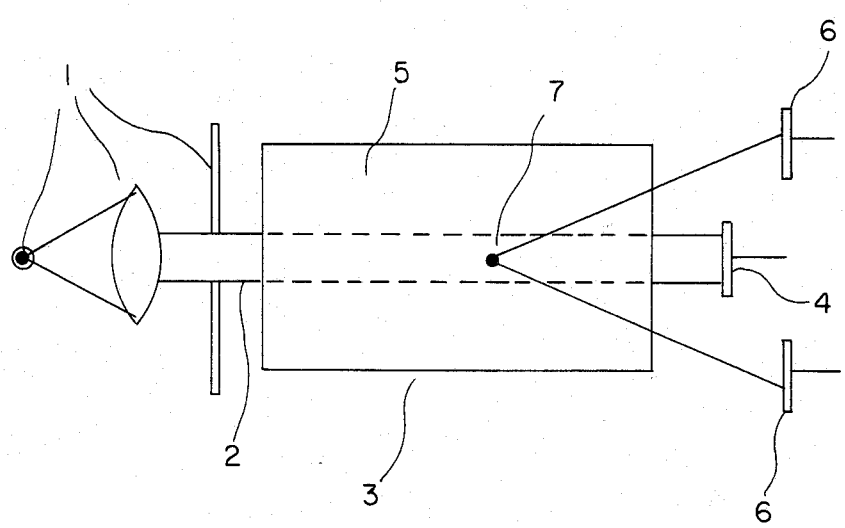
FIG. 1 shows a system for measuring scattered light.

FIG. 1 diagrammatically illustrates a system with which the breaking of oil-in-water emulsions induced by organic breakers can be controlled in the process of the invention by measurement of the turbidity of the broken water phase as a function of the quantity of organic breaker added. The system shown in FIG. 1 consists of a light source 1 producing light beam 2, a sample chamber 3, a detector 4 for transmitted light and a detector 6 for the light scattered forward, the unadsorbed light (transmitted light) emanating from light source 1 and passing through sample chamber 3 containing the sample 5 is measured by means of detector 4 for transmitted light during addition of the organic breaker and, at the same time, the light emanating from light source 1 and scattered forward by oil droplets 7 in sample 5 is measured by means of detector 6 for the light scattered forward, the measurement signals are placed in a ratio to one another after amplification, the turbidity is calculated therefrom and the result is optionally related to the quantity of breaker added and graphically recorded, and the addition of organic breaker is interrupted when the turbidity reaches a first minimum after the maximum.

Light source 1 can comprise the entire optical spectrum of wavelengths, i.e. may ber a so-called "white" light source, or may only produce light of certain wavelength ranges. Light source 1 preferably consists of a white light source which is supplied with current from a controlled power supply (not shown).

As discussed above, light beam 2 from light source 1 passes through sample chamber 3 containing liquid sample 5 of which the turbidity induced by the addition of a breaker is to be measured. Part of the light emanating from light source 1 and passing through sample chamber 3 is neither adsorbed nor scattered by the substances in sample 5. This so-called "transmitted light" is measured by detector 4 for transmitted light after passing through sample chamber 3. This measurement serves so to speak as a reference measurement and has the advantage that it is able to include the adsorbed and scattered light components of which the scattering was produced by the interface between the sample chamber and the liquid, by deposits, streaks and scratches on the wall of sample chamber 3, by adhering gas bubbles or by discoloration or solids particles in the sample. The inclusion of the scattering effects produced by these phenomena provides for correction of the scattered light measured values of which the measurement is described hereinafter.

In the breaking both of fresh oil-in-water emulsions, i.e. oil-in-water emulsions prepared for experimental purposes, and in the breaking of spent oil-in-water emulsions of the type accumulating in practice, the addition of an organic breaker produces an increase in the turbidity of the emulsion. This increase in turbidity is attributable to the face that aggregates between the organic anions of the emulsifier and the preferably cationic polymer ions of the breaker or demulsifier are formed in the broken water phase. The light emanating from light source 1 and passing through sample 5 is scattered at these macromolecular aggregates. At high emulsifier or demulsifier concentrations, it is even possible macroscopically to observe tubidity in the broken water phase. As more organic breaker is added, there is a rapid reduction in turbidity. This is attributable to coalescence of the oil droplets which are now no longer emulsified in the aqueous phase and the resulting reduction in the total number of oil particles. A reduction in turbidity may also be macroscopically observed at relatively high concentrations.

According to the invention, the light which is scattered forward by oil droplets 7 in sample 5 is measured at the same time as the transmitted light. The preferred scattering angle for measurement of the scattered light is 12°.

Detectors 4 and 6 used in the process of the invention for the transmitted light and the light scattered forward are detectors known per se and described for this purpose in the prior art. For example, the detectors may be silicon photodiodes in which the transmitted light or the light scattered forward produce low currents which are proportional to the quantity of light impinging on these diodes. In the process of the invention, the current signals produced at the particular detectors 4 and 6 are placed in a ratio to one another after amplification. The results then obtained electronically can optionally be related to the quantity of breaker added and graphically recorded by a plotter. The curve optionally recorded can be used for subsequently monitoring the breaking process.

In one preferred embodiment of the process of the invention, however, the result calculated from the ration between the two measurement signals is used for automatically interrupting the addition of organic breaker. According to the invention, this is done when the reduction in turbidity produced by the coalescence of the no longer emulsified oil droplets is superimposed on the turbidity attributable to the formation of aggregates between emulsifier anion and demulsifier cation. In practice, the superimposition of the reduction in turbidity on the increase in turbidity produces a turbidity maximum which is followed by a first turbidity minimum as more organic breaker is added. This turbidity minimum results from the fact that the reduction in turbidity in the emulsion is followed by a further increase in turbidity attributable to the fact that the coalesced oil droplets are re-emulsified again, producing an increase in the number of particles and hence in the turbidity measured. Since re-emulsification of the oil droplets is not desirable, the addition of the organic breaker has to be interrupted before the beginning of the re-emulsification, i.e. at the first minimum of the turbidity curve. The quantity of breaker added at the time of the measured turbidity minimum corresponds exactly to the quantity of organic breaker required for complete breaking of the emulsion, because the quantity of breaker added corresponds precisely at this point to the quantity of emulsifier originally present in the emulsion so that substantially complete breaking of the emulsion can be obtained.

As discussed above, it is possible to directly use the ratio between the measurement signals obtained from transmitted light and scattered light to interrupt the addition of organic breaker when the turbidity has reached a first minimum after the maximum. In another embodiment of the invention, however, it is also possible to manually interrupt the addition of organic breaker when the curve recorded by a plotter, which reproduces the turbidity profile as a function of the quantity of breaker added, reaches a first minimum after the turbidity maximum.

The process of the invention for controlling the breaking of oil-in-water emulsions induced by organic breakers and more especially for determination of the optimal quantity of breaker required for complete breaking by measurement of the turbidity of the broken water phase as a function of the quantity of organic breaker added has the advantage over the processes known from the prior art in that the "end point" determination is not affected by discoloration of the emulsion or by relatively large aggregates or particles in the emulsion. The optimal breaker dosage required for complete breaking of the emulsion can be determined simply, accurately and reproducibly by determining the first tubidity minimum after the turbidity maximum in the emulsion and interrupting the addition or organic breaker manually or fully automatically at that point. Accordingly, the process of the invention not only provides for fully automatic determination of the optimal breaker dosage, it also enables addition of the organic breaker to be continuously controlled automatically. It is thus superior to state-of-the-art processes simply through elimination of the trial-and-error determination of the end point. In addition, the optimal breaker dosage can be determined much more accurately through easy-to-measure parameters readily accessible through the process of the invention. It is thus possible to reliably avoid the overdosage of the breaker repeatedly observed in the use of prior art techniques.

The invention is illustrated but not limited by the following Examples.

The residual oil content in the broken water phase was used as the approximate value for the result of the demulsification obtained. The petroleum extractables (PE) obtained in the broken water phase were determined in accordance with DIN 38409 H 17/H 18. The test arrangement was as follows:

A 1 liter glass beaker was filled with 600 ml of the emulsion to be broken and continuously stirred at 500 r.p.m. by means of a magnetic stirrer. The length of the stirring rod was 50 mm.

The instrument used to measure turbidity was a Monitek model 25/34 immersion concentration meter, having the basic components shown in FIG. 1.

The measured value recorder, type 25 (immersion probe), was fixed to a support. The immersion depth of the probe was adjusted, i.e. all measurements were carried out at the same immersion depth of the probe.

A turbidimeter was connected to a plotter for recording the measured values (turbidity against quantity of breaker added). At a constant stirring speed of the magnetic stirrer, the particular organic breaker was added dropwise at predetermined time intervals or in a slow, continuous flow.

Samples were taken of the untreated, i.e. unbroken, emulsion and for monitoring the individual broken water phases. In the broken water phases, the petroleum ether solubles (PE) were determined in accordance with the DIN specification given above after standing for 30 minutes.

EXAMPLE 1

A mineral-oil-containing, water-miscible cooling and lubricating emulsion for the machining of steel and cast iron was broken using the test arrangement described above. The breaker used was a polyamine corresponding to the following general formula

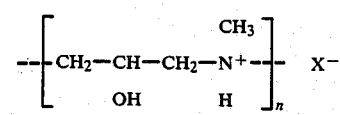

with n equal to a number that results in an average molecular weight of $0.1 \times 10^6$. The test parameters were as follows:

pH value of the untreated emulsion: 9.1
PE content of the untreated emulsion: 11,900 mg/l
Quantity of breaker added: 0.02 to 1% by vol=0.02 to 1.14% by weight
Addition of breaker: dropwise by pipetee at intervals of 30 seconds.

Figure 2:
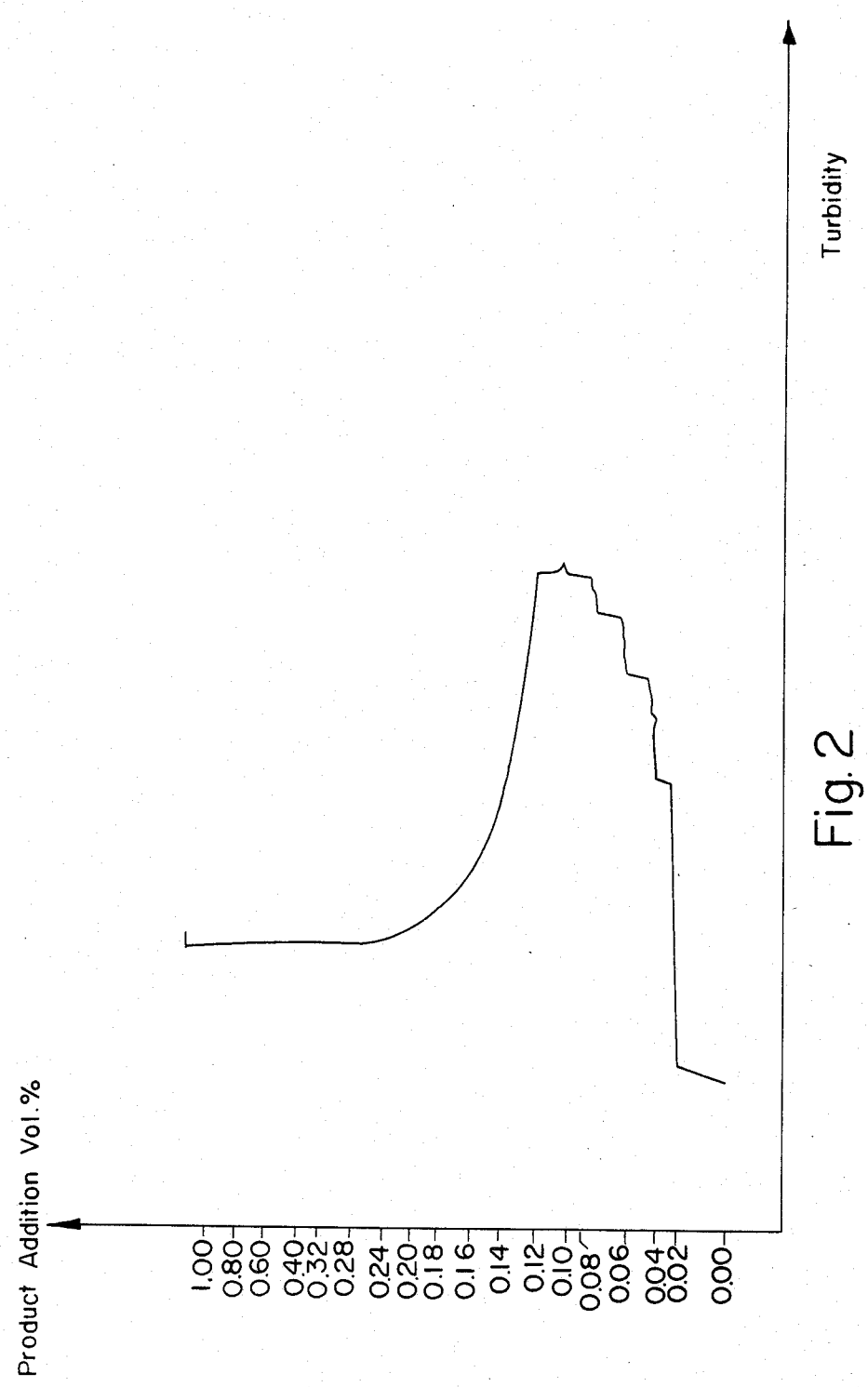
FIGS. 2-5 show examples of turbidity profiles recorded by the system of FIG. 1 as a function of the quantity of organic breaker added.

FIG. 2 shows the curve recorded by a plotter with a paper feed of 10 mm/min. over the entire test duration of 14 minutes.

Table 1 below in association with FIG. 2 shows the quantity of petroleum ether solubles (PE) in dependence upon the quantity of breaker added (product addition):

TABLE 1

| Product addition (% by vol) | FIG. 2 Petroleum ether solubles (PE) (mg/l) |
|---|---|
| — | 11,900 |
| 0.06 | 7,700 |
| 0.12 | 2,408 |
| 0.16 | 2,100 |
| 0.20 | 1,600 |
| 1.00 | 2,000 |

Result:

The rise of the curve clearly reflects the step function produced by the dropwise addition of the organic breaker. The turbidity maximum is situated at about 0.1% by volume breaker, the turbidity decreasing rapidly for a dosage of 0.12% by volume of the breaker. The sharply descending turbidity curve changes into a curve reflecting slightly increasing residual turbidity. Even with very large additions of the breaker (up to 1% by volume), no further sharp rise in the curve is discernible.

Measurements of the residual oil content (determined as the "PE value") in the broken water phase show that, at 1600 mg/l, the PE content is at its lowest for an addition of 0.2% by volume of breaker. The optimum breaker dosage is thus in the vicinity of the first tubidity minimum after the turbidity maximum of the emulsion.

EXAMPLE 2

A spent, mineral-oil-containing deep-drawing emulsion from the manufacture of aluminum cans was broken using the test arrangement described above. The breaker used was a polyamine corresponding to the following general formula

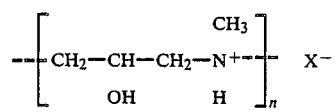

with an average molecular weight of $0.15 \times 10^6$. The pH value of the untreated emulsion was 8.5; the PE content of the untreated emulsion was determined as 39,510 mg/l. The breaker was added in quantities of from 0.02 to 0.2% by volume, corresponding to 0.02 to 0.23% by weight. The breaker was added dropwise by pipette at intervals of 30 seconds. The other test parameters correspond to those in Example 1.

Figure 3:
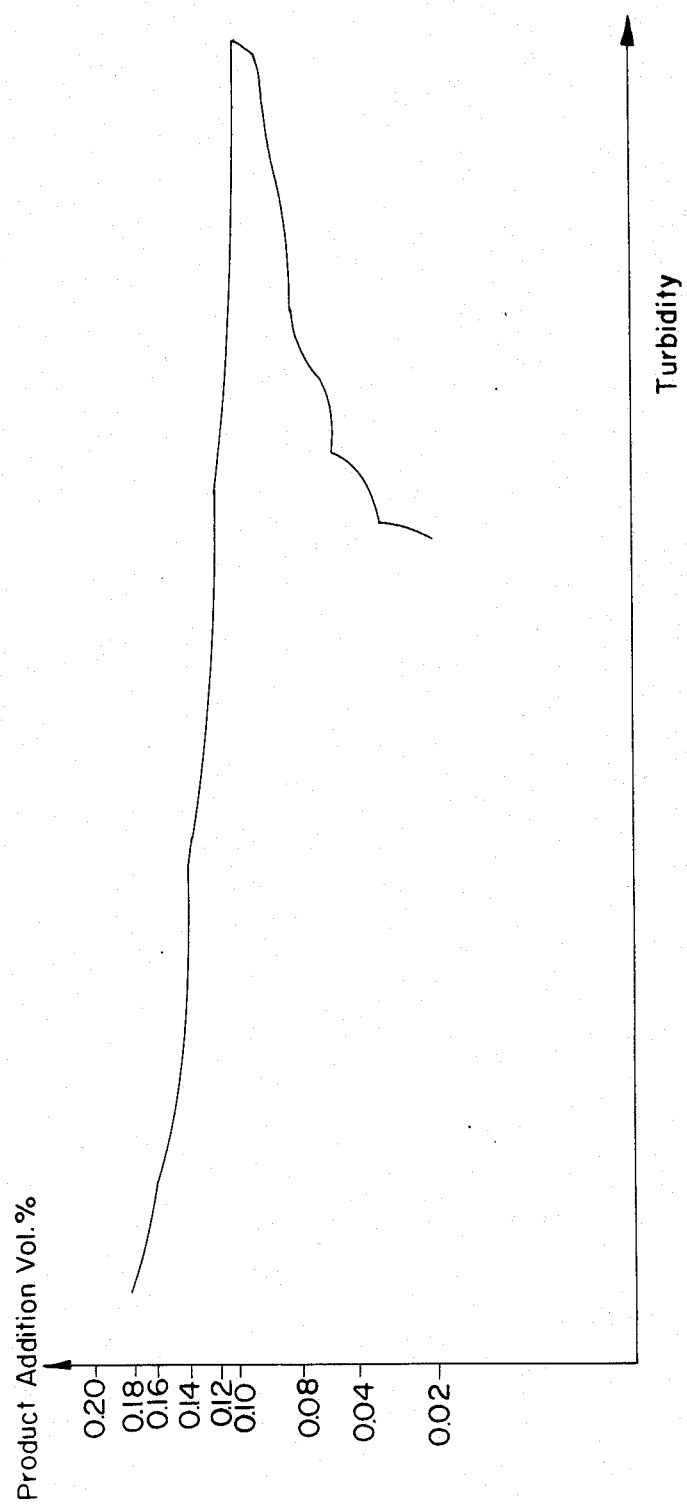

The turbidity measured as a function of the breaker dosage is shown in the curve in FIG. 3.

Table 2 below, in association with FIG. 3, shows the quantity of petroleum ether solubles (PE) in dependence upon the quantity of breaker added (product addition):

TABLE 2

| | FIG. 3 |
|---|---|
| Product addition (% by vol) | Petroleum ether solubles (PE) (mg/l) |
| — | 39,510 |
| 0.12 | 400 |
| 0.16 | 164 |
| 0.18 | 108 |
| 0.20 | 170 |

Result:

The rise of the turbidity curve again clearly reflects the step function. The turbidity maximum is reached at a breaker dosage of 0.1% by volume. Beyond a breaker dosage of 0.12% by volume, the turbidity curve descends sharply. Beyond a breaker dosage of 0.18% by volume, the reduction in turbidity is characterized by an increasingly smaller difference. Beyond a breaker dosage of 0.2% by volume. hardly any further change in tubidity is discernible.

The PE values determined for monitoring purposes show that (for PE values of 164 to 106 mg/l) the breaking optimum is situated in the region of a breaker dosage of 0.16 to 0.18% by volume. This is largely in accordance with the graphically determined optimum dosage.

EXAMPLE 3

Using the test arrangement described above, a spent degreasing bath which had orginally been used for cleaning steel parts and which contained anionic and nonionic surfactants was broken by means of a condensate of o-toluidine and formaldehyde having an average molecular weight of approximately 50,000. The pH value of the emulsion before breaking was 6.4. After foreign oils had been skimmed off, the PE content of the untreated emulsion was determined as 3,134 mg/l. The breaker was added in quantities of from 0.08 to 2.5% by volume, corresponding to 0.1 to 3.05% by weight. The breaker was continuously added dropwise by pipette.

Figure 4:
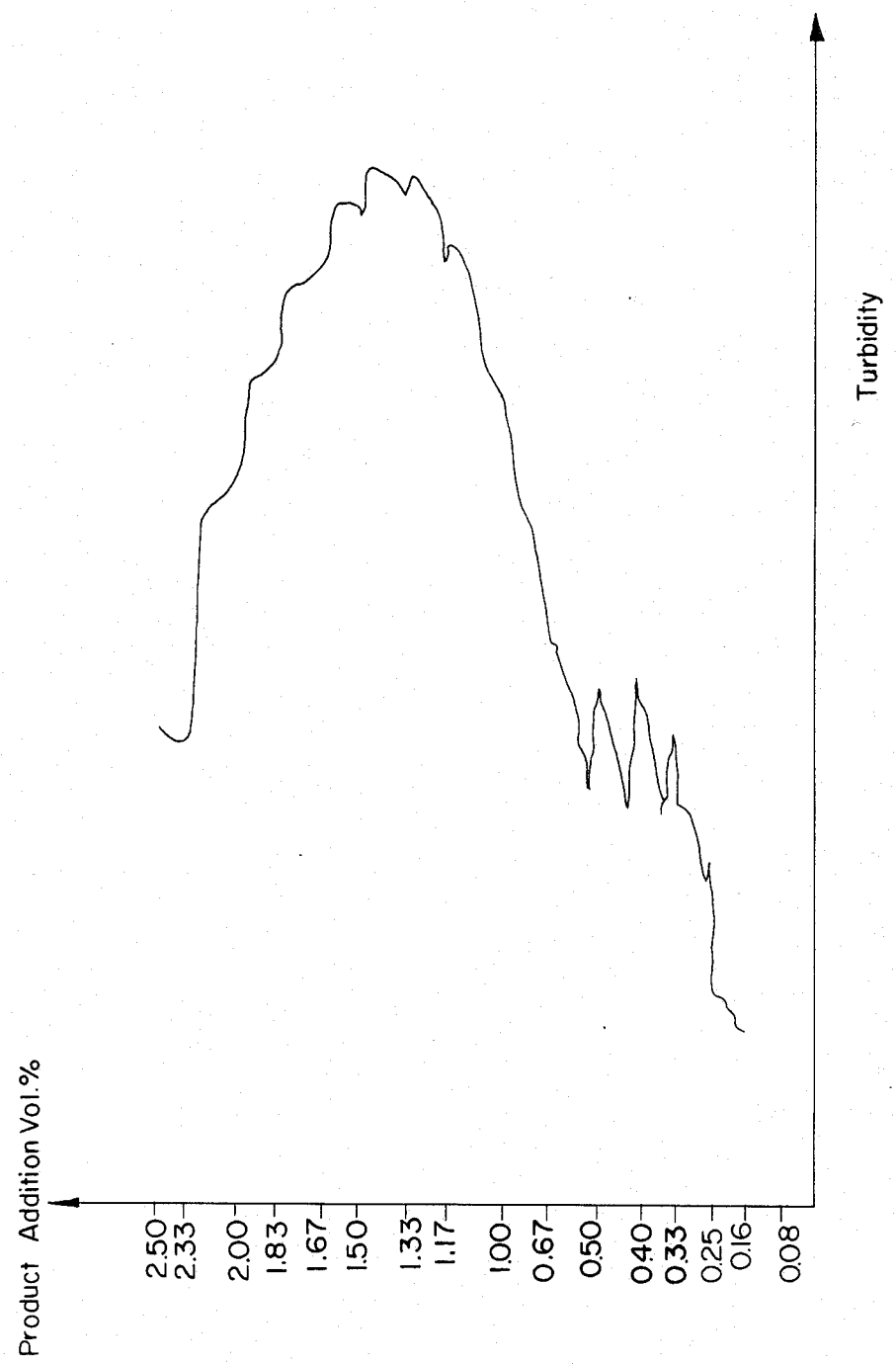

The results of the turbidity measurement are shown in FIG. 4.

Table 3 below, in association with FIG. 4, shows the quantity of petroleum ether solubles (PE) in dependence upon the quantity of breaker added (product addition):

TABLE 3

| | FIG. 4 |
|---|---|
| Product addition (% by vol) | Petroleum ether soluble (PE) (mg/l) |
| — | 3,134 |
| 0.25 | 361 |
| 0.33 | 150 |
| 0.40 | 119 |
| 0.50 | 90 |
| 1.00 | 84 |
| 2.00 | 78 |
| 2.33 | 68 |

Result:

The curve in FIG. 4 shows the steady increase in turbidity on addition of the organic breaker. The turbidity maximum is reached with a breaker dosage of 1.5% by volume. The further addition of organic breaker produces a step-by-step reduction in turbidity reflected in sagging of the curve. The turbidity minimum is reached at a breaker dosage of 2.33% by volume, the addition of more breaker producing a slight rise in the turbidity curve. Accordingly, the breaker dosage is optimal in this region. The further addition of breaker produces no further significant change in the residual turbidity.

Determination of the PE value for monitoring purposes revealed a minimum of the PE value of 68 mg/l for a breaker addition of 2.33% by volume (see above). This is largely in accordance with the graphically determined optimum of the breaker dosage.

COMPARISON EXAMPLE

A mixture of various spent degreasing baths and cooling lubricant concentrates from the metal surface treatment plant of a car factory with a pH value of 8.7 and a PE content of the untreated emulsion of 8,000 mg/l (after foreign oil had been skimmed off) was broken by means of a polyamine corresponding to the following general formula

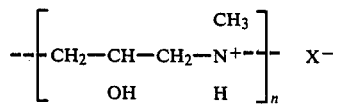

(average molecular weight approx. 75,000). The organic breaker was added dropwise by pipette in quantities of 0.02 to 0.7% by volume (corresponding to 0.02 to 0.8% by weight). The other parameters correspond to those in Examples 1 to 3. The end point of the breaker addition was determined on the one hand by the process according to the invention and, on the other hand, visually.

Figure 5:
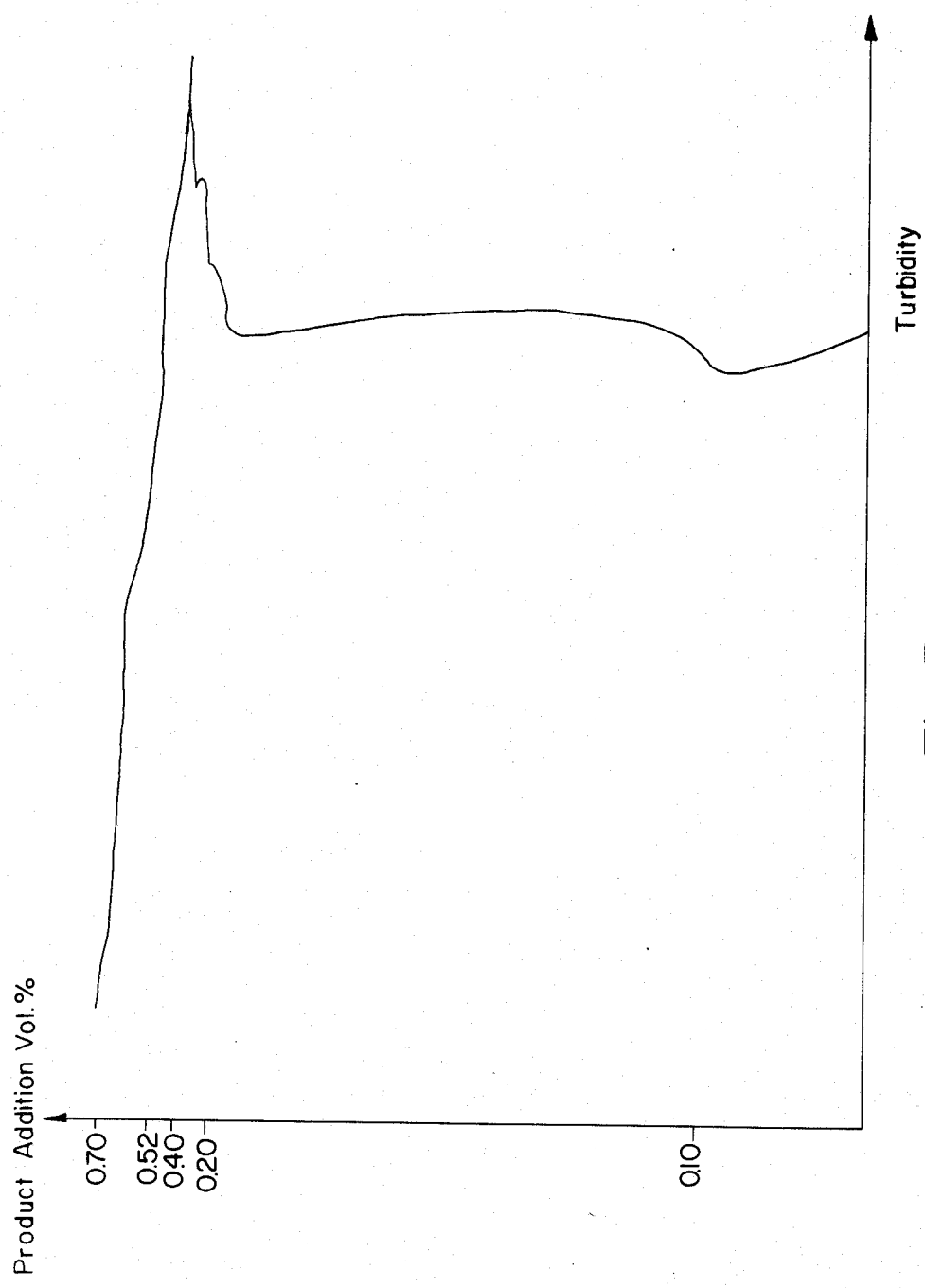

The result of the turbidity measurement is shown in FIG. 5.

Table 4 below, in association with FIG. 5, shows the quantity of petroleum ether solubles (PE) in dependence upon the quantity of breaker added (product addition):

TABLE 4

FIG. 5

| Product addition (% by vol) | Petroleum ether solubles (PE) (mg/l) |
|---|---|
| — | 8,000 |
| 0.1 | 7,000 |
| 0.2 | 150 |
| 0.52 | 80 |
| 0.7 | 150 |

Result:

In the visual determination of the optimal breaker dosage, the end point was reached at a breaker addition of 0.7% by volume. A floating oil/sludge floc was formed. After standing for 30 minutes, the PE content of the broken phase was determined as 150 mg/l.

As can be seen from the curve in FIG. 5, the optimal breaker dosage required was determined (as in Examples 1 to 2) as 0.52% by volume. The PE content in the clean water phase determined for monitoring purposes, again after a standing time of 30 minutes, was 80 mg/l.

It can be concluded from this that, in the visual determination of the optimal breaker concentration, the "end point" had already been exceeding and re-emulsification of the emulsion had set in so that part of the oil was re-emulsified in the broken water phase.

In addition, it should be pointed out that the process for visual determination of the end point extends over a period of 2 days. The same applies to determination of the PE content. By contrast, the optimal breaker concentration was determined in 30 to 60 seconds by turbidity measurement.

We claim:

1. A process for controlling the breaking of an oil-in-water emulsion using an organic emulsion breaker comprising the steps of: providing an optimal dosage range for said breaker sufficient to produce reproducible results in minimal time, by,
   A. adding the organic emulsion breaker to the emulsion by slow intermittent or continuous addition to produce a broker water phase;
   B. continuously passing a beam of light through the broken water phase;
   C. continuing the slow addition of the organic emulsion breaker to the broken water phase;
   D. continuously or intermittently measuring both the unadsorbed light passing through the broken water phase and the light scattered forward by oil droplets in the broken water phase;
   E. determining from the measurements in step D. the turbidity of the broken water phase; and
   F. discontinuing the addition of organic breaker when the turbidity reaches a first minimum value following a maximum value.

2. The process of claim 1 wherein step E. is carried out by calculating a ratio between the measurements in step D, and calculating the turbidity from the ratio.

3. The process of claim 2 wherein the turbidity calculations are graphically recorded.

4. The process of claim 3 wherein the turbidity measurements are related to the quantity of organic emulsion breaker added.

5. The process of claim 1 wherein in step B. the beam of light is a beam of white light.

6. The process of claim 1 wherein the measurements of light in step D. are made using silicon photodiodes.

7. The process of claim 1 wherein the measurement of light scattered forward in step D. is measured at a scattering angle of about 12°.

8. The process of claim 1 wherein the discontinuance of the addition of the organic emulsion breaker in step F. is effected automatically.

* * * * *